United States Patent [19]

Rose

[11] Patent Number: 4,663,291

[45] Date of Patent: May 5, 1987

[54] **METHOD FOR SOLUBILIZING MICROBIAL PROTEIN OBTAINED FROM *CHLAMYDIA TRACHOMATIS***

[75] Inventor: Philip S. Rose, Bridgeton, Mo.

[73] Assignee: Becton, Dickinson and Company, Franklin Lakes, N.J.

[21] Appl. No.: 628,310

[22] Filed: Jul. 6, 1984

[51] Int. Cl.[4] .................... G09B 19/00; G01N 33/53
[52] U.S. Cl. .................................. 435/259; 435/7; 435/29; 435/804; 435/816; 435/820; 435/822; 436/510; 436/17; 436/174; 436/824; 436/825; 436/543
[58] Field of Search ............... 436/501, 510, 824, 825, 436/17, 174, 504, 543; 435/804, 816, 820, 822, 29, 259, 7

[56] References Cited

U.S. PATENT DOCUMENTS 4,206,014  6/1980  Reichert et al. ..................... 435/7
4,497,899  2/1985  Armstrong et al. ............... 436/825

OTHER PUBLICATIONS

Helenius, et al, Methods in Enzymology, vol. LVI, (1979), pp. 734-749.

*Primary Examiner*—Christine M. Nucker
*Assistant Examiner*—Stephen C. Wieder
*Attorney, Agent, or Firm*—James R. McBride

[57] ABSTRACT

A method of specimen treatment preparatory to conducting an immunoassay is disclosed whereby a microbial protein is solubilized by a detergent at elevated temperatures and in the presence of an alkali or alkaline earth metal ion. At elevated temperatures, the detergent is soluble. However, at lower temperatures, the presence of the metal ion renders the detergent insoluble so that it is prevented from interacting in the immunoassay procedure. A specific application is in the solubilization of the principal outer membrane protein of *Chlamydia trachomatis*.

24 Claims, No Drawings

METHOD FOR SOLUBILIZING MICROBIAL PROTEIN OBTAINED FROM *CHLAMYDIA TRACHOMATIS*

TECHNICAL FIELD

This invention relates generally to a method for solubilizing proteins, and especially microbial proteins and protein complexes. More particularly, the invention relates to the use of detergents for the solubilization of protein to express the protein's antigenic properties without destroying the ability to detect the protein antigen in an immunoassay.

BACKGROUND OF THE INVENTION

Detergents have long been recognized as reagents for solubilizing many biochemicals, particularly microbial proteins and protein complexes. This ability is useful for liberating or exposing antigens in the proteins which subsequently may be detected by immunoassay techniques. Unfortunately, however, detergent in an antigen solution inhibits immunoassay by preventing the binding of the antigen to a solid phase immobilized antibody. Heretofore, no practical, inexpensive method has been available for eliminating this adverse effect of detergent on immunoassay. Simply diluting the sample is unsatisfactory. For example, if the immunoassay sample is diluted after solubilization so that the concentration of detergent no longer affects the assay procedure, the concommitant reduction in antigen concentration results in an antigen level which is below the assay threshold sensitivity. Similarly, increasing the initial concentration of antigen in the immunoassay sample such that the concentration of antigen after dilution is above the sensitivity threshold is often not practical, as sample specimens are often of necessity small. There is thus a need in the art for a method of detergent solubilization of proteins which does not simultaneously inhibit immunoassay procedures.

A specific application where detergents can be used beneficially is in the solubilization of the principal outer membrane protein of *Chlamydia trachomatis.* This microorganism is one of the two species of the genus *Chlamydiaceae,* order *Chlamydiales.* The other species is *Chlamydia psittaci. Chlamydia trachomatis* in its some 15 various strains is the etiologic agent for a number of human ocular and genital diseases, including trachoma, inclusion conjunctivitis, lymphogranuloma venereum, "nonspecific" or nongonococcal urethritis and proctitis. *C. trachomatis* infection is pervasive throughout the general population. It has been estimated, for instance, that *C. trachomatis* is accountable for several million cases per year of nongonococcal urethritis.

Since *C. trachomatis* mediated disease is widespread, a reliable, simple and inexpensive test for the organism's presence is highly desirable and of great importance so that proper treatment can be undertaken. The only serological test in current use is the microimmunofluorescence test. This test, however, requires that the strains of *C. trachomatis* be used as serological test antigen. In addition, the facilities for conducting this test are available in only a limited number of laboratories throughout the world. The test is very laborious, time consuming and difficult to perform.

SUMMARY OF THE INVENTION

The present invention relates to a method of specimen treatment preparatory to conducting an immunoassay, and is particularly useful in the preparation of microbial cell protein specimens such as those of the principal outer membrane protein of *Chlamydia trachomatis.* It has been discovered that this particular protein is a species-specific antigen and is thus useful in an immunoassay test for the presence of the organism in an infected individual.

Before cell proteins of organisms such as *C. trachomatis* can be used in an immunoassay, the cell wall containing the protein must be altered so that an appropriate antibody will recognize the protein. Treatment with a detergent has been found effective for this purpose. Of particular value in cell protein solubilization are salts of the ionic detergent lauryl sulfate. To prevent interference of the detergent with the later-performed immunoassay, the method of the invention provides for the inclusion of alkali or alkaline earth metal ion in the detergent solution. At high temperatures, the detergent is soluble in the presence of such ions. At lower temperatures, such as room temperature, the detergent precipitates out and may be optionally removed prior to performing the immunoassay.

Generally, the invention is a method for preparing microbial proteins for immunoassay, comprising: providing an aqueous solution which includes a protein-solubilizing quantity of a detergent and a compound having an alkali or alkaline earth metal ion as a cation, the compound functioning as a temperature dependent precipitating compound by causing the detergent to precipitate from the solution at room temperature or slightly above, but having no effect on detergent solubility at elevated temperatures, placing a specimen sample of microbial protein in the solution and mixing to form a sample solution, heating the sample solution to an elevated temperature, incubating the sample at the elevated temperature for a sufficient time for protein solubilization to occur, cooling the sample solution to a temperature sufficiently low to precipitate the detergent, and assaying the sample solution for the presence of antigen.

DETAILED DESCRIPTION OF THE INVENTION

The method of the invention involves the use of a temperature dependent precipitating agent for removing a protein-solubilizing quantity of detergent from an immunoassay specimen sample. Detergents are very effective protein solubilizing agents, particularly for microbial cell proteins such as the principal outer membrane protein of *Chlamydia trachomatis.* However, because they interfere with an immunoassay by inhibiting the binding of antigen, detergents must be effectively removed from the sample solution prior to performing the assay.

It has been discovered that the inclusion in the sample solution of a compound containing an alkali or alkaline earth metal ion greatly reduces the aqueous solubility of a detergent, such as a lauryl sulfate, at room temperature or slightly above (i.e., at or below about 30° C.), but has little or no effect on solubility at elevated temperatures. Because of their ability to effect temperature dependent precipitation of detergent, these compounds will sometimes hereinafter be referred to as precipitating compounds. It is to be understood that this connotation does not mean that the compounds themselves precipitate, only that they cause precipitation of detergent. By alkali or alkaline earth metals is meant the elements of Groups I and II of the Periodic Table, which include, among others, lithium, sodium, potassium, magnesium, calcium and barium. Thus, for example, an aqueous solution of a sodium or lithium lauryl sulfate and potassium ion can be used to solubilize microbial protein at elevated temperature. The solution then is cooled to about room temperature or slightly above, causing the detergent to be precipitated out. The detergent may optionally be removed by centrifugation or filtration. Whether or not the precipitated detergent is removed, the immunoassay is then performed on the sample of protein without interference from the detergent. Since the precipitating compound plays no role in the invention until the cooling step, it may be added to the solution after the protein is solubilized, rather than combined initially with the detergent.

Suitable detergents for use in the invention include lauryl sulfates such as sodium dodecyl sulfate and lithium dodecyl sulfate. Generally, detergent is present in the solution in concentrations of from about 0.01 percent weight per volume to about 2.0 percent weight per volume. Desirably, the concentration is from about 0.01 to about 1.0 percent weight per volume, with from about 0.05 to about 0.1 percent weight per volume preferred.

The precipitating compound is present in the solution in concentrations of from about 0.01 M to about 2.0 M. Desirably, the concentration is from about 0.01 M to about 1.0 M, with from about 0.05 M to about 1.0 M preferred. Any water soluble compound having an alkali or alkaline earth metal ion as a cation can be used. The compound may be, for example, a phosphate, chloride or carbonate salt. The selection of a particular precipitating compound is influenced by the particular detergent used. For example, sodium dodecyl sulfate is precipitated most easily at room temperature by sufficient concentrations of potassium, calcium or barium ion, while lithium dodecyl sulfate, in addition to the above ions, will be adequately precipitated by ions of magnesium and sodium.

The aqueous solution of detergent and precipitating compound is added to a specimen sample, such as a cervical or urethral swab. The sample is mixed thoroughly with the aqueous solution of detergent and precipitating compound to form a sample solution. In mixing the sample solution at room temperature the detergent remains undissolved. The solution, with the undissolved detergent, is heated from room temperature to a temperature of from about 60° C. to about 120° C., and maintained at that temperature for a period of from about 5 min. to about 30 min. At this incubation temperature, the detergent dissolves and solubilizes the microbial protein, exposing the antigen for immunoassay purposes.

After incubation, the solution is cooled rapidly using an ice bath or other suitable means to a temperature sufficiently low to allow precipitation of the detergent. Alternatively, the solution may be cooled slowly until it reaches room temperature. A suitable buffer such as a phosphate (e.g., 0.2 M sodium phosphate, 0.1% weight per volume bovine serum albumin, pH 7.4) may be added before or after the incubation. The buffer maintains the pH of the solution between about 6.5 and about 8.0. After cooling, the precipitated detergent may be removed, or left in the sample. If left in, the detergent has little or no effect on the immunoassay since it is not in solution.

As noted above, a particular use for the method of the invention is in the solubilization of *Chlamydia trachomatis*. The principal outer membrane protein of *C. trachomatis* comprises about 60% of the total associated outer membrane protein of the microorganism, and has a size or subunit molecular weight of between 38,000 and 44,000 daltons, with a mean molecular weight of 39,500 daltons. Hereinafter for ease in reference, this principal outer membrane protein group of C. trachomatis will be referred to as MP 39.5, signifying "major outer membrane protein having a mean subunit molecular weight of 39,500 daltons." MP 39.5 is a species-specific antigen, in that, when tested against *C. trachomatis* antibodies drawn from all of the serotypes thereof, this protein reacts with species specificity. As an antigen, MP 39.5 provides a basis for the identification of all the *C. trachomatis* serotypes.

Species-specific antibodies against an antigen such as MP 39.5 can be generated by suitable inoculation procedures with laboratory animals such as mice and/or rabbits. The animal-generated antibodies may be used in assays for infection in other mammals. These assays may be conducted using well-known procedures for assaying the presence of bacterial antigen in the infected subject. Once a supply of monospecific antibodies has been secured from antigen-inoculated laboratory animals, either direct or indirect assay procedures can be undertaken with specimens secured from mammals suspected of harboring infections. Assay techniques such as enzymelinked immunoabsorbent assay or radioimmunoassay are suitable for these purposes.

In a direct assay procedure, monospecific antibody against the antigen is attached covalently or noncovalently to a solid phase support system. As is customary in these techniques, the support system may be glass, plastic or the like. The solid phase support with attached monospecific antibody may be incubated with a specimen prepared according to the method of the invention and previously secured from an individual suspected of having an infection.

Monospecific antibody, which has been previously radiolabeled or conjugated with enzyme by known techniques, is then equilibrated against the support system. Any antigen present in the specimen and which has been bound to the antibody on the support system will in turn bind to the radiolabeled or enzyme-conjugated antibody. If radiolabeled antibody is used, the relative residual radioactivity in the sample then may be determined. This value is compared to specimens that have been determined to be free of the antigen. In the event enzyme-conjugated antibody is used, a substrate, specific for the enzyme, is added to the solid support reaction mixture and the resultant color change is recorded spectrophotometrically. This color change is compared to samples known to be free of the antigen. The presence of an antigen such as MP 39.5 in the mammalian specimens thus can be assayed directly.

Alternatively, indirect assay procedures can be used. Specifically, the antigen may be covalently or noncovalently bound to a suitable solid phase support system. A specimen from the individual suspected of having an infection is prepared as described above. The specimen then is mixed with a known quantity of radiolabeled or enzyme-conjugated antibody against the antigen, previously secured from a laboratory animal source. The specimen/antibody mixture then may be incubated with a solid support system and its bound antigen.

The radioactivity of the solid support system is measured, or color development in the enzyme-conjugated system is measured, and compared to specimens similarly treated as standards and which do not contain antigen.

The ability of the clinical sample suspected of containing a particular microorganism to inhibit the binding of the radiolabeled or enzyme-conjugated antibodies to the solid support reveals the presence, or absence, of the antigen in the clinical specimen. Any demonstrated inhibition indicates the presence of infection.

Other suitable assay methods and variations will be apparent to those skilled in such assay techniques.

Example 1 illustrates the method of the invention, utilizing C. trachomatis MP 39.5. Table I compares a control immunoassay to one in which the specimen is prepared according to the method of the invention.

EXAMPLE I

To a 450 sample of *Chlamydia trachomatis* stock solution in phosphate buffer (0.2 M sodium phosphate, 0.1% weight per volume bovine serum albumin, pH 7.4) was added potassium chloride in quantity sufficient to bring the potassium ion concentration in the sample to 0.1 M. Approximately 50 of a 1% weight per volume solution of SDS (sodium dodecyl sulfate) in water was then added, followed by heating the sample to 100° C. in a heating block. The sample was incubated at this temperature for 10 minutes and then cooled to room temperature in an ice bath to precipitate the SDS. Immunoassays at stock dilutions of 1:1, 1:2, 1:4, 1:8 and 1:16 were then performed without removal of the precipitated detergent. A control was also prepared by the same procedure except that the addition of potassium chloride was omitted. The results in Table I show that a positive indication of Chlamydia can be obtained at much higher dilutions using the invention, when compared to a control not employing the precipitating agent. This demonstrates a considerable gain in sensitivity.

While the best mode and the preferred embodiments have been disclosed herein as required by the Patent Statutes, the invention should not be construed as being limited thereto or thereby. Rather, it is intended that modifications and changes can be made to the invention without departing from the scope thereof.

TABLE I

| Chlamydia Stock[1] Dilution | EIA RESULTS[2] Treated as per Example | Untreated (Control) |
|---|---|---|
| 1:16 | .53 | 0 |
| 1:8 | .94 | 0 |
| 1:4 | 1.31 | .11 |
| 1:2 | 1.65 | .27 |
| Undiluted | 1.81 | .45 |

[1]neat, $5 \times 10^7$ elementary bodies/ml in 0.02 M sodium phosphate buffer.
[2]expressed as S/N ratio of optical density of absorbance at 450 nm.

I claim:

1. A method for preparing microbial proteins obtained from *Chlamydia trachomatis* for immunoassay, comprising:

mixing a specimen sample of microbial protein obtained from *Chlamydia trachomatis* with an aqueous solution of a protein-solubilizing quantity of an ionic detergent having an alkali or alkaline earth metal ion as a cation to form a sample solution;

incubating the sample at an elevated temperature for a sufficient time for protein solubilization to occur; and cooling the sample solution in the presence of a compound having an alkali or alkaline earth metal ion as a cation, the compound functioning as a temperature dependent precipitating compound thus causing the detergent to precipitate from the solution at room temperature or slightly above, but having no effect on detergent solubility at elevated temperatures, said cation of said compound being different than the cation of said detergent.

2. The method of claim 1, wherein the detergent is present in the sample solution in an amount of from about 0.01 percent weight per volume to about 2.0 percent weight per volume.

3. The method of claim 2, wherein the precipitating compound is present in the solution in an amount of from about 0.01 molar to about 2.0 molar.

4. The method of claim 3, wherein the precipitating compound has a cation selected from the group consisting of ions of sodium, potassium, calcium, barium, and magnesium.

5. The method of claim 4, wherein the sample solution is incubated at a temperature of from about 60° C. to about 120° C. for a period of from about 5 to about 30 minutes.

6. The method of claim 5, wherein the detergent is present in the solution in an amount of from about 0.01 percent weight per volume to about 1.0 percent weight per volume.

7. The method of claim 6, wherein the compound is present in a solution in an amount of from about 0.01 molar to about 1.0 molar.

8. The method of claim 7, wherein the solution contains a buffer to maintain the pH of the solution between about 6.5 and about 8.0.

9. The method of claim 8, wherein the detergent is a lauryl sulfate.

10. The method of claim 9, wherein the precipitating compound is a water soluble salt.

11. The method of claim 10, wherein the detergent is sodium dodecyl sulfate and the precipitating compound has a cation selected from the group consisting of potassium, calcium and barium.

12. The method of claim 11, wherein the solution is incubated at a temperature of about 100° C. for a period of about 10 minutes..

13. The method of claim 12, wherein the precipitating compound is potassium chloride and is present in the solution in an amount of from about 0.05 molar to about 1.0 molar.

14. The method of claim 13, wherein the detergent is present in an amount of from about 0.05 percent weight per volume to about 0.1 percent weight per volume.

15. The method of claim 10, wherein the detergent is lithium dodecyl sulfate and the precipitating compound has a cation selected from the group consisting of calcium, barium, potassium, sodium and magnesium.

16. The method of claim 15, wherein the solution is incubated at a temperature of about 100° C. for a period of about 10 minutes.

17. The method of claim 16, wherein the precipitating compound is potassium chloride and is present in the solution in an amount of from about 0.05 molar to about 1.0 molar.

18. The method of claim 17, wherein the detergent is present in an amount of from about 0.05 percent weight per volume to about 0.1 percent weight per volume.

19. The method of claim 15, wherein the sample solution is assayed for the presence of antigen.

20. The method of claim 20, wherein the solution is assayed by means of radioimmunoassay fluorescense immunoassay, or enzyme immunoassay.

21. The method of claim 20, wherein the precipitation compound is added to the sample solution prior to the incubation step.

22. The method of claim 19, wherein the precipitating compound is added to the sample solution after the incubation step.

23. The method of claim 21, wherein the precipitating compound is added to the sample solution prior to the incubation step.

24. The method of claim 20, wherein the precipitating compound is added to the sample solution after the incubation step.

* * * * *